United States Patent [19]

Morozowich

[11] 4,304,926
[45] Dec. 8, 1981

[54] PHENACYL-TYPE ESTERS OF PGE-TYPES COMPOUNDS

[75] Inventor: Walter Morozowich, Kalamazoo, Mich.

[73] Assignee: The Upjohn Company, Kalamazoo, Mich.

[21] Appl. No.: 497,244

[22] Filed: Aug. 14, 1974

[51] Int. Cl.³ .......................................... C07C 177/00
[52] U.S. Cl. ................................................. 560/121
[58] Field of Search .................... 260/468 D; 560/121

[56] References Cited

U.S. PATENT DOCUMENTS 3,812,179  5/1974  Bundy ................................... 26/514
3,984,454 10/1976  Skubulla et al. ..................... 260/468

FOREIGN PATENT DOCUMENTS 2322655 11/1974  Fed. Rep. of Germany ...... 260/468

OTHER PUBLICATIONS

Shriner et al., Organic Compounds, p. 197 (1950).
Fieser et al., Reagent for Organic Synthesis, p. 1201.
McOmie, Protective Groups in Organic Chemistry, p. 199 (1972).

Primary Examiner—Robert Gerstl
Attorney, Agent, or Firm—Lawrence T. Welch; Morris L. Nielsen

[57] ABSTRACT

Phenacyl-type esters of PGE$_2$, PGE$_1$, and 13,14-dihydro-PGE$_1$ and their 15-methyl, 16,16-dimethyl, and 17-phenyl analogs, including the respective 15(R)epimers, are disclosed, represented by the formula

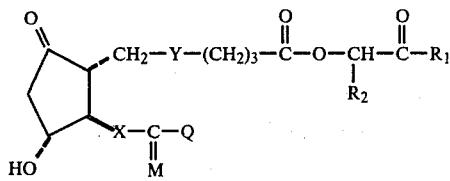

wherein M is

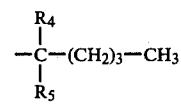

wherein $R_3$ is hydrogen or methyl; wherein Q is

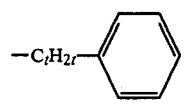 (1)

wherein each of $R_4$ and $R_5$ is hydrogen or methyl, being the same or different, or

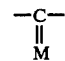 (2)

wherein the moiety —$C_tH_{2t}$— represents a valence bond or alkylene of one to 10 carbon atoms, inclusive, with one to 7 carbon atoms, inclusive, between

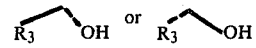

and the phenyl ring; wherein $R_1$ is phenyl, p-bromophenyl, p-biphenylyl, p-nitrophenyl, p-benzamidophenyl, or 2-naphthyl; wherein $R_2$ is hydrogen or benzoyl; and wherein (a) X is —CH$_2$CH$_2$— or trans—CH=CH— and Y is —CH$_2$CH$_2$—, or (b) X is trans—CH=CH— and Y is cis—CH=CH—. The products are useful for the same pharmacological and medical purposes as the corresponding prostaglandins and analogs, and are also useful as a means for obtaining highly purified products.

30 Claims, No Drawings

PHENACYL-TYPE ESTERS OF PGE-TYPES COMPOUNDS

BACKGROUND OF THE INVENTION

This invention relates to novel ester derivitives of prostaglandin E₂ (hereinafter identified as "PGE₂"), PGE₁, and 13,14-dihydro-PGE₁ and their 15-methyl, 16-(or 16,16-di)-methyl, and phenyl-substituted analogs, including the respective 15(R)epimers, and to processes for producing them.

PGE₂ is represented by the formula:

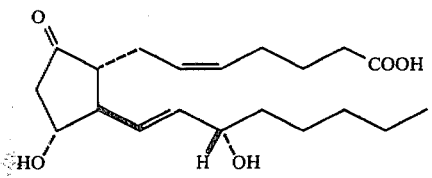

A systematic name for pGE₂ is 7-{3α-hydroxy-2β-[(3S)-3-hydroxy-trans-1-octenyl]-5-oxo-1α-cyclopentyl}-cis-5-heptenoic acid. PGE₂ is known to be useful for a variety of pharmacological and medical purposes, for example labor induction and abortion in pregnant animals, including humans, menstrual regulation in both pregnant and non-pregnant animals, including humans, reduction and control of gastric secretion, and as a hypotensive agent to reduce blood pressure in mammals, including humans. See Bergstrom et al., Pharmacol. Rev. 20, 1 (1968) and references cited therein. As to racemic PGE₂, see for example W. P. Schneider, Chem. Commun. 304 (1969).

The 15(S)-15-methyl-PGE₂ analog and its 15(R) epimer are represented by the formula:

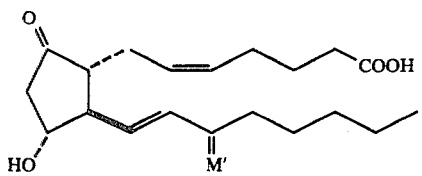

wherein M' is

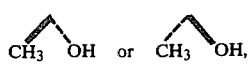

following the usual convention wherein broken line attachment of hydroxy to the side chain at carbon 15 indicates the natural or "S" configuration and solid line attachment of hydroxy indicates the epi or "R" configuration. See for example Nugteren et al., Nature 212, 38 (1966) and Cahn, J. Chem. Ed. 41, 116 (1964). The 15(S)-15-methyl- and 15(R)-15-methyl-PGE₂ analogs in their optically active and racemic forms are known. See for example U.S. Pat. No. 3,728,382. These analogs are also useful for the above-described pharmacological purposes.

The 16-(or 16,16-di)methyl-PGE₂ analogs and their 15(R) epimers are represented by the formula:

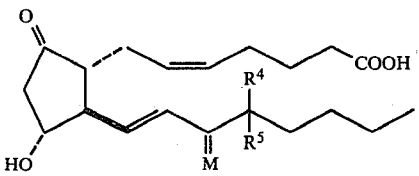

wherein M is

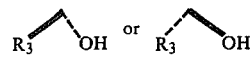

wherein $R_3$ is hydrogen or methyl, and wherein each of $R_4$ and $R_5$ is hydrogen or methyl, being the same or different. These 16-methyl- and 16,16-dimethyl-PGE₂ analogs and their 15(R) epimers in their optically active and racemic forms are available or can be prepared by methods known in the art. See for example German Pat. No. 2,217,044, Derwent Farmdoc No. 71483T.

The phenyl-substituted PGE₂ analogs and their 15(R) epimers are represented by the formula:

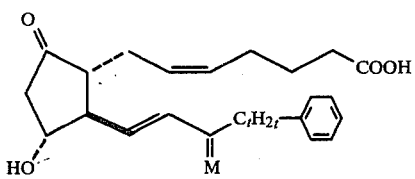

wherein M is

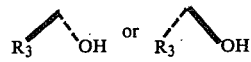

wherein $R_3$ is hydrogen or methyl, and wherein $C_tH_{2t}$ represents a valence bond or alkylene of one to 10 carbon atoms, inclusive, with one to 7 carbon atoms, inclusive, between

and the phenyl ring. These substituted analogs and their 15(R) epimers in their optically active and racemic forms are available or can be prepared by methods known in the art. See for example German Pat. No. 2,154,309, Derwent Farmdoc Nol 31279T.

PGE₁ is represented by the formula:

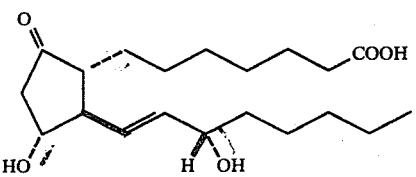

and the PGE₁ analogs are represented similarly to the PGE₂ analogs above except that cis—CH═CH— in the carboxy acid side chain of formulas II, III, and IV is replaced by —CH₂CH₂—. These PGE₁ compounds are available or are prepared by methods known in the art. See for example E. J. Corey et al., J. Am. Chem. Soc. 90, 3245 (1968) and 92, 2586 (1970); U.S. Pat. nos.

3,069,322, and 3,728,382, 3,598,858, J. E. Pike et al., J. Org. Chem. 34, 3552 (1969); G. L. Bundy et al., Ann. N.Y. Acad. Sci. 180, 76 (1971); and German Pat. No. 2,154,309, Derwent Farmdoc No. 31279T.

13,14-Dihydro-PGE$_1$ is represented by the formula:

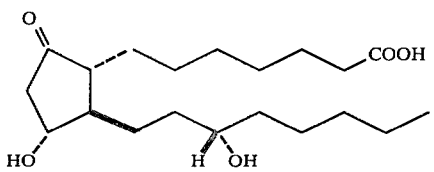

and the 13,14-dihydro-PGE$_1$ analogs are represented similarly to the PGE$_2$ analogs above except that cis—CH=CH— in the carboxy acid side chain and trans—CH=CH— in the alkyl-terminated side chain of formulas II, III, and IV are replaced by —CH$_2$CH$_2$—. These 13,14-dihydro-PGE$_1$ compounds are available or are prepared by methods known in the art. See for example U.S. Pat. Nos. 3,711,528, 3,728,382, 3,776,938; and German Pat. No. 2,154,309, Derwent Farmdoc No. 31279T.

All of the above prostaglandin-type compounds are known to be useful for a variety of pharmacological and medical purposes, and the esters of this invention are useful for the same purposes.

Esters of the above compounds are known, wherein the hydrogen atom of the carboxyl group is replaced by a hydrocarbyl or substituted hydrocarbyl group. Among these are the methyl ester of PGE$_2$ (B. Samuelsson, J. Biol. Chem. 238, 3229 (1963)), the methyl ester of 15-methyl-PGE$_2$ (E. W. Yankee et al., J. Am. Chem. Soc. 94, 3651 (1972)), the methyl ester of 13,14-dihydro-PGE$_1$ (U.S. Pat. No. 3,598,858), the decyl ester of PGE$_2$ (Belgian Pat. No. 765,732, Derwent Farmdoc No. 67580S), the 2-phenoxyethyl ester of PGE$_2$ (Belgian Pat. No. 766,294, Derwent Farmdoc No. 39011T), the phenyl and alkyl-phenyl esters of PGE$_2$ (British Spec. No. 1,282,661, Derwent Farmdoc No. 67438R), the p-(1,1-3,3-tetramethyl-butyl)-phenyl ester of PGE$_2$, the α (and β-)-naphthyl ester of PGE$_2$, and the 5,6,7,8-tetrahydro-2-naphthyl ester of PGE$_2$ (Belgian Pat. No. 775,106, Derwent Farmdoc No. 33705T) the methyl ester of 16,16-dimethyl-PGE$_2$ (German Pat. No. 2,217,044, Derwent 71483T), and the methyl and phenyl esters of 17-phenyl-18,19,20-trinor-PGE$_2$ (German Pat. No. 2,154,309, Derwent 31279T).

SUMMARY OF THE INVENTION

It is a purpose of this invention to provide novel ester derivatives of PGE$_2$, PGE$_1$, and 13,14-dihydro-PGE$_1$ and their 15-methyl, 16-(or 16,16-di)methyl, and phenyl-substituted analogs, including the respective 15(R) epimers. It is a further purpose to provide each esters in a free-flowing crystalline form. It is still a further purpose to provide novel processes for preparing these esters.

The presently described phenacyl-type esters include compounds represented by the generic formula:

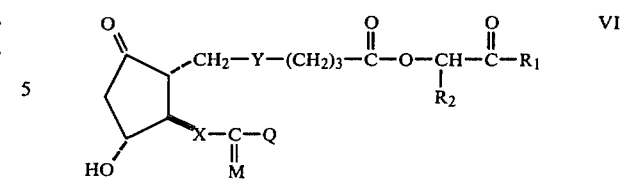   VI wherein M is

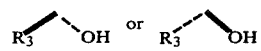

wherein R$_3$ is hydrogen or methyl; wherein Q is

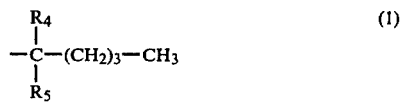   (1)

wherein each of R$_4$ and R$_5$ is hydrogen or methyl, being the same or different, or

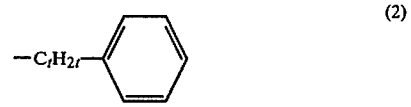   (2)

wherein the moiety C$_t$H$_{2t}$- represents a valence bond or alkylene of one to 10 carbon atoms, inclusive, with one to 7 carbon atoms, inclusive, between

and the phenyl ring; wherein R$_1$ is phenyl, p-bromophenyl, p-biphenyl, p-nitrophenyl, p-benzamidophenyl, or 2-naphthyl; wherein R$_2$ is hydrogen or benzoyl; and wherein (a) X is —CH$_2$CH$_2$— or trans—CH=CH— and Y is —CH$_2$CH$_2$—, or (b) X is trans—CH=CH— and Y is cis—CH=CH—.

Thus, in the presently described esters, the group

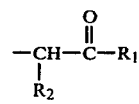

is exemplified by:

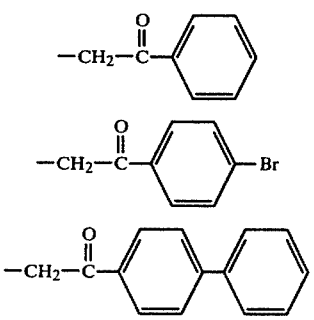

-continued

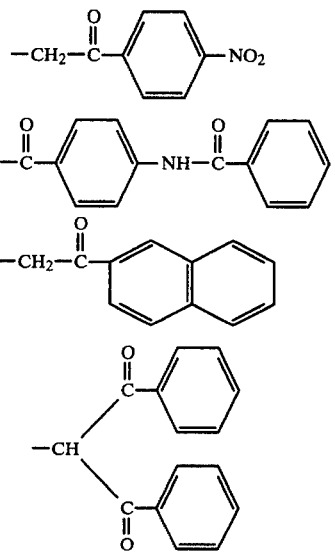

For example, PGE$_2$, phenacyl ester, is represented by formula VI when M is

X is trans—CH=CH—, Y is cis—CH=CH—, and

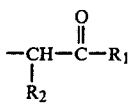

is A, i.e.

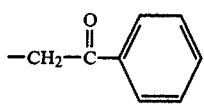

and is conveniently identified herein as the PGE$_2$ ester of formula VI-A. Racemic compounds are designated by the prefix "racemic" or "dl;" when that prefix is absent, the intent is to designate an optically active compound. For example, racemic 15-methyl-PGE$_1$, p-benzamidophenacyl ester, corresponds to formula VI wherein M is

X is trans—CH=CH—, Y is —CH$_2$CH$_2$—, and

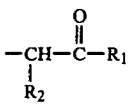

is E, i.e.

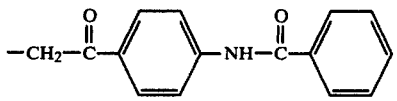

including of course not only the optically active isomer represented by formula VI but also its mirror image.

The novel formula-VI compounds and corresponding racemic compound of this invention are each useful for the same purposes as described above for PGE$_2$ and are used for those purposes in the same manner known in the art, including oral, sublingual, buccal, rectal, intravaginal, intrauterine, or topical administration.

For many applications these novel prostaglandin esters which I have obtained from certain specified phenacyl-type halides have advantages over the corresponding known prostaglandin compounds. Thus, these phenacyl-type esters are surprisingly stable compounds having outstanding shelf-life and thermal stability. In contrast to the acid form of these prostaglandins, these esters are not subject to acid-catalyzed decomposition either by elimination of water or by epirmerization. Thus these compounds have improved stabilty either in solid, liquid, or solution form. In oral administration these esters have shown surprisingly greater efficacy than the corresponding free acids or lower alkyl esters, whether because of longer duration of biological activity or because of improved lipophilicity and absorption is not certain. These esters offer a further advantage in that they have low solubility in water and the body fluids and are therefore retained longer at the site of administration.

A particularly outstanding advantage of many of these phenacyl-type esters is that they are obtained in free-flowing crystalline form, generally of moderately high melting point, in the range 50°-130° C. This form is especially desirable for ease of handling, administering, and purifying. These crystals are highly stable, for example showing practically no decomposition at accelerated storage tests, in comparison with liquid alkyl esters or the free acids. This quality is advantageous because the compound does not lose its potency and does not become contaminated with decomposition products.

These crystalline esters also provide a means of purifying PGE$_2$, PGE$_1$, 13,14-dihydro-PGE$_1$, and their 15-methyl, 16-(or 16,16-di)methyl, or phenyl-substituted analogs, including the respective 15(R) epimers, which are first converted to one of these esters, crystallized and recrystallized until pure, and then recovered as the free acid. One method of recovering the free acid is by enzymatic hydrolysis of the ester, for example with a lipase. See German Pat. No. 2,242,792, Derwent Farmdoc No. 23047U.

A p-iodophenacyl ester of 15(S)-15-methyl-PGF$_{2\alpha}$ was useful for X-ray crystallographic structure determination, E. W. Yankee et al., J. Am. Chem. Soc. 94, 3651 (1972). Various phenacyl esters have been useful for characterizing aliphatic acids because of their sharp melting points, Shriner and Fuson, "Systematic Identification of Organic Compounds", 3rd Ed., pp. 154-157 (1948).

Especially preferred of the novel compounds of this invention are those compounds which are in free-flowing crystalline form, for example:
 phenacyl ester of PGE$_2$
 p-bromophenacyl ester of PGE$_2$
 p-phenylphenacyl ester of PGE$_2$
 p-nitrophenacyl ester of PGE$_2$
 p-benzamidophenacyl ester of PGE$_2$
 p-naphthoylmethyl ester of PGE$_2$
 α-benzoylphenacyl ester of PGE$_2$ p-phenylphenacyl ester of 15(S)-15-methyl-PGE$_2$
p-nitrophenacyl ester of 15(S)-15-methyl-PGE$_2$
p-nitrophenacyl ester of 17-phenyl-18,19,20-trinor-PGE$_2$
p-phenylphenacyl ester of PGE$_1$
p-phenylphenacyl ester of 16,16-dimethyl-PGE$_1$
p-phenylphenacyl ester of 17-phenyl-PGE$_1$
p-phenylphenacyl ester of 13,14-dihydro-18,19,20-trinor-PGE$_1$ The phenacyl-type esters of PGE$_2$, PGE$_1$, 13,14-dihydro-PGE$_1$ and their 15-methyl, 16-(or 16,16-di)-methyl, or phenyl-substituted analogs, including the respective 15(R) epimers encompassed by formula VI wherein

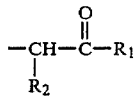

is defined by ester groups A through G are produced by the reactions and procedures described and exemplified hereinafter. For convenience, the prostaglandin or prostaglandin analog is referred to as "the PG compound." the term "phenacyl" is used in a generic sense, including also substituted phenyl and naphthyl derivatives.

Various methods are available for preparing these esters. Thus, by one method, the PG compound is converted to a sodium salt by method known in the art and reacted with an appropriate phenacyl halide in a solvent.

Preferred, however, is the method of simply mixing the PG compound with a phenacyl halide, preferably the bromide, and a tertiary amine in a solvent and letting the reaction proceed at room temperature (about 20° to 30° C.). The course of the reaction is readily followed by sampling the mixture and subjecting the samples to thin layer chromatogrphy, usually being complete within 0.25–4.0 hr. Thereafter the reaction mixture is worked up to yield the ester following methods described herein or known in the art, for example the product being purified by silica gel chromatography.

Examples of the phenacyl-type halides useful for this purpose are: phenacyl bromide, p-bromophenacyl bromide, p-phenylphenacyl bromide, p-nitrophenacyl bromide, p-benzamidophenacyl bromide, 2-bromo-2'-acetonaphthone, and 2-bromo-1,3-diphenyl-1,3-propanedione. In using these reagents the usual precautions are taken to avoid their lachrymatory effects.

Examples of suitable tertiary amines are triethylamine, diethylmethylamine, diisopropylethylamine, dimethylisobutylamine, and dimethylaniline.

Examples of suitable solvents are acetonitrile, dioxane, and tetrahydrofuran, N,N-dimethylformamide, and dimethylsulfoxide.

The phenacyl halide is preferably used in equivalent amounts or in excess to insure that all of the PG compound is converted to ester. Excess phenacyl halide is separated from the product by methods described herein or known in the art, for example by chromatography.

Solid esters are converted to a free-flowing crystalline form on crystallization from a variety of solvents, including ethyl acetate, tetrahydrofuran, methanol, ethanol, and acetone, by cooling or evaporating a saturated solution of the ester in the solvent or by adding a miscible non-solvent such as diethyl ether, hexane, or water. The crystals are then collected by conventional techniques, e.g. filtration or centrifugation, washed with a small amount of solvent, and dried under reduced pressure. They may be dried in a current of warm nitrogen or argon, or by warming up to about 75° C., taking care not to exceed the melting point. Although the crystals are normally pure enough for many applications, they may be recrystallized by the same general techniques to achieve improved purity after each recrystallization.

DESCRIPTION OF THE PREFERRED EMBODIMENTS

The invention can be more fully understood by the following examples.

All temperatures are in degrees centigrade.

Silica gel chromatography, as used herein, is understood to include chromatography on a column packed with silica gel, elution, collection of fractions, and combination of those fractions shown by thin layer chromatography (TLC) to contain the desired product free of starting material and impurities.

"TLC", herein, refers to thin layer chromatography.

EXAMPLE 1 PGE$_2$, Phenacyl Ester (Formula VI-A wherein M is

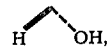

Q is n-pentyl, X is trans-CH=CH—, and Y is cis—CH=CH—)

A mixture of PGE$_2$ (0.50 g.), phenacyl bromide (0.440 g.) and 0.37 ml. of diisopropylethylamine in 10 ml. of acetonitrile is left standing for one hour at about 25° C. The mixture is diluted with 200 ml. of ethyl acetate and extracted with aqueous 0.1 N. phosphate buffer at pH 7.5 and then water. The organic phase is dried over sodium sulfate and concentrated under reduced pressure to a crude residue. The residue is subjected to silica gel chromatography, eluting with ethyl acetate-hexane (1:1) followed by ethyl acetate. The residue obtained by concentration of selected fractions is crystallized from ethyl acetate-hexane as the title compound, white free-flowing crystals, 0.510 g., m.p. 57.3°–58.8°, having R$_f$ 0.65 (TLC on silica gel in ethyl acetate).

EXAMPLE 2 PGE$_2$, p-Bromophenacyl Ester (Formula VI-B wherein M is

Q is n-pentyl, X is trans—CH=CH—, and Y is cis—CH=CH—)

Following the procedure of Example 1 but using 0.50 g. of PGE$_2$, 0.80 g. of p-bromophenacyl bromide, and 0.37 ml. of diisopropylethylamine in 10 ml. acetonitrile kept for 2 hrs. at about 25° C., there is obtained a crude residue. This residue is subjected to silica gel chromatography, eluting with ethyl-acetate-hexane (1:1) followed by ethylacetate. The residue obtained by concentration of selected fractions is crystallized from ethyl acetate-hexane as the title compound, white free-flowing crystals, 0.628 g., m.p. 83.3°–87.5° C., having R$_f$ 0.4 (TLC on silica gel in ethylacetate-hexane (7:3)).

EXAMPLE 3   PGE$_2$, p-Phenylphenacyl Ester
(Formula VI-C wherein M is

Q is n-pentyl, X is trans—CH=CH—, and Y is cis—CH=CH—)

Following the procedure of Example 1 but using 0.242 g. of PGE$_2$, 0.720 g. of p-phenylphenacyl bromide, and 0.40 ml. of diisopropylethylamine, there is obtained a crude residue. This residue is subjected to silica gel chromatography, eluting with 100 ml. of ethyl acetate-hexane (1:3) followed by 100 ml. of ethyl acetate-hexane (1:1), 200 ml. of ethyl acetate and finally 200 ml. of ethyl acetate-acetone (3:2). The residue obtained by concentration of selected fractions is crystallized from ethyl acetate-hexane as the title compound, white free-flowing crystals, 0.328 g., m.p. 98.6°–100.9°, having R$_f$ 0.4 (TLC on silica gel in ethyl acetate-hexane (4:1)).

EXAMPLE 4   PGE$_2$ p-Nitrophenacyl Ester
(Formula VI-D wherein M is

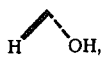

Q is n-pentyl, X is trans-CH=CH—, and Y is cis—CH=CH—)

Following the procedure of Example 1 but using 0.100 g. of PGE$_2$, 0.100 g. of p-nitrophenacyl bromide, and 0.100 ml. of diisopropylethylamine in 10 ml. of acetonitrile for 15 min. at about 25° C., there is obtained a crude residue. This residue is subjected to silica gel chromatography, eluting with chloroform-acetonitrile (9:1). The residue obtained by concentration of selected fractions is crystallized from ethyl acetate-hexane as the title compound, white free-flowing crystals, 0.088 g., m.p. 65.9°–67.2° C., having R$_f$ 0.7 (TLC on silica gel in chloroform-acetonitrile (1:1)).

EXAMPLE 5   PGE$_2$, p-Benzamidophenacyl Ester
(Formula VI-E wherein M is

Q is n-pentyl, X is trans—CH=CH—, and Y is cis—CH=CH—)

Following the procedure of Example 1 but using 0.352 g. of PGE$_2$, 0.410 g. of p-benzamidophenacyl bromide, and 1.0 ml. of diisopropylethylamine in 20 ml. of acetonitrile held for 2 hr. at about 25° C., there is obtained a crude residue. This residue is subjected to silica gel chromatography, eluting with ethyl acetate-hexane (7:3) followed by tetrahydrofuran. The residue obtained by concentration of selected fractions is crystallized from hot ethanol-water (1:1) as the title compound, white free-flowing crystals, 0.39 g., m.p. 125.8°–129.0° C., having R$_f$ 0.42 (TLC on silica gel in ethyl acetate-acetic acid (97:3)).

EXAMPLE 6   PGE$_2$, 2-Naphthoylmethyl Ester
(Formula VI-F wherein M is

Q is n-pentyl, X is trans—CH=CH—, and Y is cis—CH=CH—)

Following the procedure of Example 1 but using 0.500 g. of PGE$_2$, 0.80 g. of 2-bromo-2'-acetonaphthone, and 0.37 ml. of diisopropylethylamine in 10 ml. of acetonitrile kept for 2 hr. at about 25° C., there is obtained a crude residue. This residue is subjected to silica gel chromatography, eluting with ethyl acetate-hexane (1:1) followed by ethyl acetate. The residue obtained by concentration of selected fractions is crystallized from ethyl acetate-hexane, as the title compound, white free-flowing crystals, 0.658 g., m.p. 64.8°–66.3° C., having R$_f$ 0.4 (TLC on silica gel in ethyl acetate-hexane (7:3)).

EXAMPLE 7   PGE$_2$, α-Benzoylphenacyl Ester
(Formula VI-G wherein M is

Q is n-pentyl, X is trans—CH=CH—, and Y is cis—CH=CH—)

Following the procedure of Example 1 but using 0.352 g. of PGE$_2$, 0.306 g. of 2-bromo-1,3-diphenyl-1,3-propanedione, and 0.129 g. of diisopropylethylamine, there is obtained a crude residue. This residue is subjected to silica gel chromatography, eluting with chloroform-acetonitrile (9:1). The residue obtained by concentration of selected fractions is crystallized from ethyl acetate-hexane as the title compound, white free-flowing crystals, 0.165 g., m.p. 103.8°–106.5° C., having R$_f$ 0.5 (TLC on silica gel in chloroformacetonitrile (7.3)).

EXAMPLE 8   15(S)-15-Methyl-PGE$_2$,
p-Phenylphenacyl Ester (Formula VI-C wherein M is

Q is n-pentyl, X is trans—CH=CH—, and Y is cis—CH=CH—)

Following the procedure of Example 1 but using 0.163 g. of 15-methyl-PGE$_2$, 0.611 g. of p-phenylphenacyl bromide, and 0.154 ml. of diisopropylethylamine in 12 ml. of acetonitirle, held for 1 hr. at about 25° C., there is obtained a crude residue. This residue is subjected to silica gel chromatography, eluting with ethyl acetate. The residue obtained by concentration of selected fractions is crystallized from ethyl acetate-hexane as the title compound, white free-flowing crystals, 0.153 g., m.p. 90.3°–91.3° C., having R$_f$ 0.7 (TLC on silica gel in ethyl acetate-acetic acid (97:3)).

EXAMPLE 9   15(S)-15-Methyl-PGE$_2$,
p-Nitrophenacyl Ester (Formula VI-D wherein M is

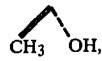

Q is n-pentyl, X is trans—CH=CH—, and Y is cis—CH=CH—)

Following the procedure of Example 1 but using 0.163 g. of 15-methyl-PGE$_2$, 0.543 g. of p-nitrophenacyl bromide, and 0.154 ml. of diisopropylethylamine in 10 ml. of acetonitrile, held for one hour at about 25° C., there is obtained a crude residue. This residue is subjected to silica gel chromatography, eluting with ethyl acetate-chloroform (1:1) followed by ethyl acetate-acetone (4:1). The residue obtained by concentration of selected fractions, an oil, is further purified on a preparative TLC silica gel plate, eluting with acetone-methanol (4:1). There is obtained the title compound, a pale-yellow free-flowing crystalline solid, 0.117 g., m.p. 115.8°–118.8° C., having $R_f$ 0.6 (TLC on silica gel in ethyl acetate).

EXAMPLE 10  15(R)-15-Methyl-PGE$_2$, p-Nitrophenacyl Ester (Formula VI-D wherein M is

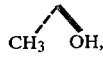

Q is n-pentyl, X is trans—CH=CH— and Y is cis-CH=CH—)

Following the procedure of Example 1 but using 0.205 g. of 15(R)-15-Methyl-PGE$_2$, 0.274 g. of p-nitrophenacyl bromide and 0.145 ml. of diisopropylethylamine, there is obtained a crude, viscous, brown residue. This residue is subjected to silica gel chromatography, eluting with chloroform-acetonitrile (1:1). The residue obtained by concentration of selected fractions, colorless liquid, 0.290 g. is the title compound, a colorless liquid, 0.290 g., having $R_f$ 0.5 (TLC on silica gel in chloroform-acetonitrile (1:2)).

EXAMPLE 11  16,16-Dimethyl-PGE$_2$, Phenacyl Ester (Formula VI-A wherein M is

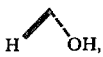

Q is

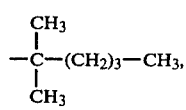

X is trans—CH=CH—, and Y is cis—CH=CH—)

Following the procedure of Example 1 but using 0.190 g. of 16,16-dimethyl-PGE$_2$, 0.099 g. of α-bromoacetophenone, and 0.065 g. of diisopropylethylamine in 15 ml. of acetonitrile, stirred for one hour at about 25° C., there is obtained a crude residue. This residue is dissolved in 20 ml. of acetonitrile, mixed with 100 ml. of 0.1 N. citric acid buffer at pH 2.5, and extracted with 100 ml. of ethyl acetate. The organic phase is dried and concentrated to yield the title compound, a light yellow gum, having mass spectral peaks at 627, 552, 543, 537, 453, 399, 227, 105, and 77, and having $R_f$ 0.64 (TLC on silica gel in ethyl acetate-acetic acid (97:3)).

EXAMPLE 12  16,16-Dimethyl-PGE$_2$, p-Phenylphenacyl Ester (Formula VI-C wherein M is

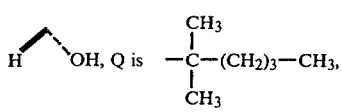

X is trans—CH=CH—, and Y is cis—CH=CH—)

Following the procedure of Example 1 but using 0.190 g. of 16,16-dimethyl-PGE$_2$, 0.550 g. of 2-bromo-4'-phenylacetophenone, and 0.297 g. of diisopropylamine in 15 ml. of acetonitrile, stirred for one hour at about 25° C., there is obtained a crude residue. This residue is subjected to silica gel chromatography, eluting with hexane followed by ethyl acetatehexane (1:1). The residue obtained by concentration of selected fractions is the title compound, a light yellow gum, having mass spectral peaks at 619, 529, 497, 475, 407, and 181, and having $R_f$ 0.73 (TLC on silica gel in ethyl acetate-acetic acid (97:3))

EXAMPLE 13  17-Phenyl-18,19,20-trinor-PGE$_2$, p-Nitrophenacyl Ester, (Formula VI-D wherein M is

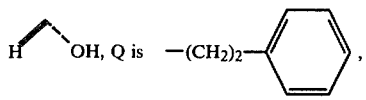

X is trans—CH=CH—, and Y is cis—CH=CH—)

Following the procedure of Example 1 but using 0.210 g. of 17-phenyl-18,19,20-trinor-PGE$_2$, 0.275 g. p-nitrophenacyl bromide, and 0.146 ml. of diisopropylethylamine, there is obtained a crude, light brown, viscous residue. This residue is subjected to silica gel chromatography, eluting with chloroform-acetonitrile (1:1). The residue obtained by concentration of selected fractions is a colorless semisolid, which is crystallized from 5 ml. ethylacetate by dilution with 5 ml. hexane to yield the title compound, white free-flowing crystals, 0.250 g., m.p. 74.7°–76.5° C., having $R_f$0.45 (TLC on silica gel in chloroform-acetonitrile (1:1)).

EXAMPLE 14  PGE$_1$, p-Phenylphenacyl Ester (Formula VI-C wherein M is

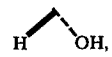

Q is n-pentyl, X is trans—CH=CH—, and Y is —CH$_2$CH$_2$—)

A mixture of PGE$_1$ (0.555 g.), p-phenylphenacyl bromide (0.731 g.) and 0.34 ml. of diisopropylethylamine in 10 ml. of acetonitrile is shaken until completely miscible, then left standing one hour at about 25° C. The mixture is concentrated under reduced pressure to a crude residue and subjected to silica gel chromatography, eluting with ethyl acetate and then with acetonitrile. The residue obtained by concentration of selected fractions, 0.682 g., is recrystallized from ethyl acetate-hexane as the title compound, white free-flowing crystals 0.668 g., m.p. 112.2°–113.2° C., having $R_f$0.7 (TLC on silica gel in ethyl acetate).

EXAMPLE 15  16,16-Dimethyl-PGE$_1$, p-Phenylphenacyl Ester (Formula VI-C wherein M is

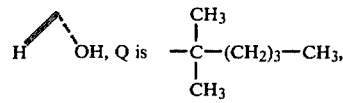

X is trans—CH=CH—, and Y is —CH$_2$CH$_2$—)

Following the procedure of Example 14 but using 0.30 g. fo 16,16-dimethyl-PGE$_1$, 0.75 g. of p-phenylphenacyl bromide, and 0.5 ml. of diisopropylethylamine in 12 ml. of acetonitrile, there is obtained a crude residue. This residue is subjected to silica gel chromatography, eluting with 33 to 60% ethyl acetate in Skellysolve B. The residue obtained by concentration of selected fractions, is crystallized from ethyl ether-Skellysolve B as the title compound, 0.175 g., free-flowing crystals, m.p. 77°-8° C., having NMR peaks at 7.3-8.1, 5.66, 5.36, 3.25-4.3, 0.9, and 0.85δ, and having $R_f$ 0.60 (TLC on silica gel in ethyl acetate).

EXAMPLE 16  17-Phenyl-18,19,20-trinor-PGE$_1$, p-Phenylphenacyl Ester (Formula VI-C wherein M is

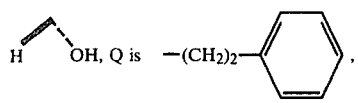

X is trans—CH=CH—, and Y is —CH$_2$CH$_2$—)

Following the procedure of Example 14 but using 0.20 g. of 17-phenyl-18,19,20-trinor-PGE$_1$, 0.6 g. of p-phenylphenacyl bromide, and 0.4 ml. of diisopropylethylamine in 10 ml. of acetonitrile, there is obtained a crude solid residue. This residue is subjected to silica gel chromatography, eluting with 30-100% ethyl acetate in Skellysolve B. The residue obtained by concentration of selected fractions, 0.277 g., partially crystalline, is recrystallized from acetone-Skellysolve B as the title compound 0.18 g., white free-flowing needles, m.p. 112°-113° C., having $R_f$0.53 (TLC on silica gel in ethyl acetate) and infrared absorption bonds at 3360, 1745, 1715, 1685, 1600, 1240, 1165, 1125, 1095, 1075, 1005, 970, 765, 750, 700, and 695 cm$^{-1}$.

EXAMPLE 17  13,14-Dihydro-PGE$_1$, p-Phenylphenacyl Ester (Formula VI-C wherein M is

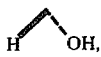

Q is n-pentyl, and X and Y are —CH$_2$CH$_2$—)

Following the procedure of Example 14 but using 2.7 g. of 13,14-dihydro-PGE$_1$, 5.0 g. of p-phenylphenacyl bromide, and 4.5 ml. of diisopropylethylamine in 110 ml. of acetonitrile, there is obtained a crude residue. This residue is subjected to silica gel chromatography, eluting with 40-75% ethyl acetate in Skellysolve B. The residue obtained by concentration of selected fractions, 3.2 g. is crystallized from ethyl acetate-Skellysolve B (1:3) as the title compound, 2.63 g., white free-flowing crystals, m.p. 89°-91° C., having infrared absorption bands at 3420, 1745, 1725, 1690, 1605, 1580, 1555, 1485, 1340, 1235, and 1165.

Following the procedures of Examples 1-17 but employing the racemic forms of the PG compounds, there are obtained the corresponding esters of racemic PG compounds.

EXAMPLES 18-112

The phenacyl-type esters of PGE$_2$, PGE$_1$, 13,14-dihydro-PGE$_1$, and their 15-methyl, 16-(or 16,16-di)-methyl, or phenylsubstituted analogs, including the respective 15(R) epimers of Tables I-XV below are obtained following the procedures of Example 1, wherein the prostaglandin compound is reacted in the presence of diisopropylethylamine with the appropriate phenacyl halide reagent listed in the Table. The crude products, obtained by concentration under reduced pressure, are purified by means described herein or known in the art, including partitioning, solvent extraction, washing, silica gel chromatography, trituration, or crystallization.

Following the procedures of Examples 18—112 but employing the racemic forms of the PG compounds, there are obtained the corresponding esters of the racemic PG compounds.

Likewise following the procedures of Examples 61-112 but employing the 15(R) forms of the PG compounds and their racemic forms, there are obtained the corresponding esters of the respective 15(R) PG compounds and their forms.

TABLE I

Esters of 15(R)-PGE$_2$ (Refer to formula VI wherein

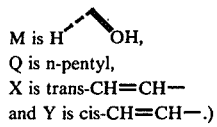

M is H OH,
Q is n-pentyl,
X is trans-CH=CH—
and Y is cis-CH=CH—.)

| Example | Phenacyl Halide | Product 15(R)-PGE$_2$ ester of formula: |
|---|---|---|
| 18 | phenacyl bromide | VI-A |
| 19 | p-bromophenacyl bromide | VI-B |
| 20 | p-phenylphenacyl bromide | VI-C |
| 21 | p-nitrophenacyl bromide | VI-D |
| 22 | p-benzamidophenacyl bromide | VI-E |
| 23 | 2-bromo-2'-acetonaphthone | VI-F |
| 24 | 2-bromo-1,3-diphenyl-1,3-propanedione | VI-G |

TABLE II

Esters of 15(S)-15-Methyl-PGE$_2$ (Refer to formula VI wherein

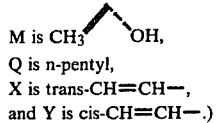

M is CH$_3$ OH,
Q is n-pentyl,
X is trans-CH=CH—,
and Y is cis-CH=CH—.)

| Example | Phenacyl Halide | Product 15(S)-15-Methyl -PGE$_2$ ester of formula: |
|---|---|---|
| 25 | phenacyl bromide | VI-A |
| 26 | p-bromophenacyl bromide | VI-B |
| 27 | p-benzamidophenacyl bromide | VI-E |
| 28 | 2-bromo-2'-acetonaphthone | VI-F |
| 29 | 2-bromo-1,3-diphenyl-1,3-propanedione | VI-G |

TABLE III

Esters of 15(R)-15-Methyl-PGE$_2$ (Refer to formula VI wherein

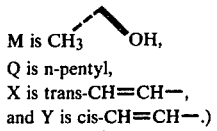

M is CH$_3$ OH,
Q is n-pentyl,
X is trans-CH=CH—,
and Y is cis-CH=CH—.)

| Example | Phenacyl Halide | Product 15(R)-15-methyl -PGE$_2$ ester of formula: |
|---|---|---|
| 30 | phenacyl bromide | VI-A |
| 31 | p-bromophenacyl bromide | VI-B |
| 32 | p-phenylphenacyl bromide | VI-C |
| 33 | p-benzamidophenacyl bromide | VI-E |
| 34 | 2-bromo-2'-acetonaphthone | VI-F |
| 35 | 2-bromo-1,3-diphenyl-1,3-propanedione | VI-G |

TABLE IV
Esters of 16,16-dimethyl-PGE$_2$ (Refer to formula VI wherein

M is 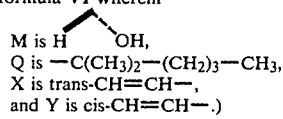

Q is —C(CH$_3$)$_2$—(CH$_2$)$_3$—CH$_3$,

X is trans-CH=CH—, and Y is cis-CH=CH—.)

| Example | Phenacyl Halide | Product 16,16-dimethyl PGE$_2$ ester of formula: |
|---|---|---|
| 36 | p-bromophenacyl bromide | VI-B |
| 37 | p-nitrophenacyl bromide | VI-D |
| 38 | p-benzamidophenacyl bromide | VI-E |
| 39 | 2-bromo-2'-acetonaphthone | VI-F |
| 40 | 2-bromo-1,3-diphenyl-1,3-propanedione | VI-G |

TABLE V
Esters of 15(R)-16,16-dimethyl-PGE$_2$ (Refer to formula VI wherein M is 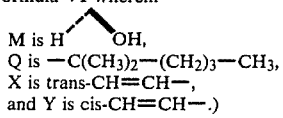

Q is —C(CH$_3$)$_2$—(CH$_2$)$_3$—CH$_3$,

X is trans-CH=CH—, and Y is cis-CH=CH—.)

| Example | Phenacyl Halide | Product 15(R)-16,16-dimethyl-PGE$_2$ ester of formula: |
|---|---|---|
| 41 | phenacyl bromide | VI-A |
| 42 | p-bromophenacyl bromide | VI-B |
| 43 | p-phenylphenacyl bromide | VI-C |
| 44 | p-nitrophenacyl bromide | VI-D |
| 45 | p-benzamidophenacyl bromide | VI-E |
| 46 | 2-bromo-2'-acetonaphthone | VI-F |
| 47 | 2-bromo-1,3-diphenyl-1,3-propanedione | VI-G |

TABLE VI
Esters of 17-Phenyl-18,19,20-trinor-PGE$_2$ (Refer to formula VI wherein M is H   OH, Q is —(CH$_2$)$_2$—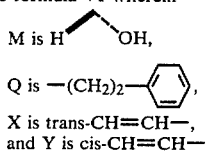, X is trans-CH=CH—, and Y is cis-CH=CH—.)

| Example | Phenacyl Halide | Product 17-phenyl-18,19,20-trinor-PGE$_2$ ester of formula: |
|---|---|---|
| 48 | Phenacyl bromide | VI-A |
| 49 | p-bromophenacyl bromide | VI-B |
| 50 | p-phenylphenacyl bromide | VI-C |
| 51 | p-benzamidophenacyl bromide | VI-E |
| 52 | 2-bromo-2'-acetonaphthone | VI-F |
| 53 | 2-bromo-1,3-diphenyl-1,3-propanedione | VI-G |

TABLE VII
Esters of 15(R)-17-Phenyl-18,19,20-trinor-PGE$_2$ (Refer to formula VI wherein M is H   OH, Q is —(CH$_2$)$_2$—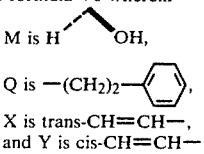, X is trans-CH=CH—, and Y is cis-CH=CH—.)

| Example | Phenacyl Halide | Product 15(R)-17-phenyl-18,19,20-trinor-PGE$_2$ ester of formula: |
|---|---|---|
| 54 | phenacyl bromide | VI-A |

TABLE VII-continued
Esters of 15(R)-17-Phenyl-18,19,20-trinor-PGE$_2$

| Example | Phenacyl Halide | Product 15(R)-17-phenyl-18,19,20-trinor-PGE$_2$ ester of formula: |
|---|---|---|
| 55 | p-bromophenacyl bromide | VI-B |
| 56 | p-phenylphenacyl bromide | VI-C |
| 57 | p-nitrophenacyl bromide | VI-D |
| 58 | p-benzamidophenyl bromide | VI-E |
| 59 | 2-bromo-2'-acetonaphthone | VI-F |
| 60 | 2-bromo-1,3-diphenyl-1,3-propanedione | VI-G |

TABLE VIII
Esters of PGE$_1$ (Refer to formula VI wherein

M is H   OH,

Q is n-pentyl,

X is trans-CH=CH—, and Y is —CH$_2$CH$_2$—.)

| Example | Phenacyl Halide | Product PGE$_1$ ester of formula: |
|---|---|---|
| 61 | phenacyl bromide | VI-A |
| 62 | p-bromophenacyl bromide | VI-B |
| 63 | p-nitrophenacyl bromide | VI-D |
| 64 | p-benzamidophenacyl bromide | VI-E |
| 65 | 2-bromo-2'-acetonaphthone | VI-F |
| 66 | 2-bromo-1,3-diphenyl-1,3-propanedione | VI-G |

TABLE IX
Esters of 15(S)-15-Methyl-PGE$_1$ (Refer to formula VI wherein

M is CH$_3$   OH,

Q is n-pentyl,

X is trans-CH=CH— and Y is —CH$_2$CH$_2$—.)

| Example | Phenacyl Halide | Product 15(S)-15-methyl-PGE$_1$ ester of formula: |
|---|---|---|
| 67 | phenacyl bromide | VI-A |
| 68 | p-bromophenacyl bromide | VI-B |
| 69 | p-phenylphenacyl bromide | VI-C |
| 70 | p-nitrophenacyl bromide | VI-D |
| 71 | p-benzamidophenacyl bromide | VI-E |
| 72 | 2-bromo-2'-acetonaphthone | VI-F |
| 73 | 2-bromo-1,3-diphenyl-1,3-propanedione | VI-G |

TABLE X

Esters of 16,16-Dimethyl-PGE₁

(Refer to formula VI wherein

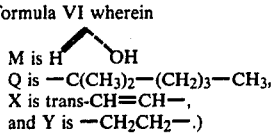

M is H  OH,
Q is —C(CH₃)₂—(CH₂)₃—CH₃,
X is trans-CH=CH—,
and Y is —CH₂CH₂—.)

| Example | Phenacyl Halide | Product 16,16-dimethyl-PGE₁ ester of formula: |
|---|---|---|
| 74 | phenacyl bromide | VI-A |
| 75 | p-bromophenacyl bromide | VI-B |
| 76 | p-nitrophenacyl bromide | VI-D |
| 77 | p-benzamidophenacyl bromide | VI-E |
| 78 | 2-bromo-2'-acetonaphthone | VI-F |
| 79 | 2-bromo-1,3-diphenyl-1,3-propanedione | VI-G |

TABLE XI

Esters of 17-Phenyl-18,19,20-trinor-PGE₁

(Refer to formula VI wherein

M is H  OH,

Q is —(CH₂)₂—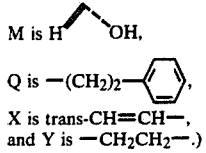,

X is trans-CH=CH—,
and Y is —CH₂CH₂—.)

| Example | Phenacyl Halide | Product 17-phenyl-18,19,20-trinor-PGE₁ ester of formula: |
|---|---|---|
| 80 | phenacyl bromide | VI-A |
| 81 | p-bromophenacyl bromide | VI-B |
| 82 | p-nitrophenacyl bromide | VI-D |
| 83 | p-benzamidophenacyl bromide | VI-E |
| 84 | 2-bromo-2'-acetonaphthone | VI-F |
| 85 | 2-bromo-1,3-diphenyl-1,3-propanedione | VI-G |

TABLE XII

Esters of 13,14-Dihydro-PGE₁

(Refer to formula VI wherein

M is H  OH,
Q is n-pentyl, and
X and Y are —CH₂CH₂—.)

| Example | Phenacyl Halide | Product 13,14-dihydro-PGE₁ ester of formula: |
|---|---|---|
| 86 | phenacyl bromide | VI-A |
| 87 | p-bromophenacyl bromide | VI-B |
| 88 | p-nitrophenacyl bromide | VI-D |
| 89 | p-benzamidophenacyl bromide | VI-E |
| 90 | 2-bromo-2'-acetonaphthone | VI-F |
| 91 | 2-bromo-1,3-diphenyl-1,3-propanedione | VI-G |

TABLE XIII

Esters of 15(S)-15-Methyl-13,14-Dihydro-PGE₁

(Refer to formula VI wherein

M is CH₃  OH,
Q is n-pentyl, and
X and Y are —CH₂CH₂—.)

| Example | Phenacyl Halide | Product 15(S)-15-methyl-13,14-dihydro-PGE₁ ester of formula: |
|---|---|---|
| 92 | phenacyl bromide | VI-A |
| 93 | p-bromophenacyl bromide | VI-B |
| 94 | p-phenylphenacyl bromide | VI-C |
| 95 | p-nitrophenacyl bromide | VI-D |
| 96 | p-benzamidophenacyl bromide | VI-E |
| 97 | 2-bromo-2'-acetonaphthone | VI-F |
| 98 | 2-bromo-1,3-diphenyl-1,3-propanedione | VI-G |

TABLE XIV

Esters of 16,16-Dimethyl-13,14-dihydro-PGE₁

(Refer to formula VI wherein

M is H  OH,
Q is —C(CH₃)₂—(CH₂)₃—CH₃, and
X and Y are —CH₂CH₂—.)

| Example | Phenacyl Halide | Product 16,16-dimethyl-13,14-dihydro-PGE₁ ester of formula: |
|---|---|---|
| 99 | phenacyl bromide | VI-A |
| 100 | p-bromophenacyl bromide | VI-B |
| 101 | p-phenylphenacyl bromide | VI-C |
| 102 | p-nitrophenacyl bromide | VI-D |
| 103 | p-benzamidophenacyl bromide | VI-E |
| 104 | 2-bromo-2'-acetonaphthone | VI-F |
| 105 | 2-bromo-1,3-diphenyl-1,3-propanedione | VI-G |

TABLE XV

Esters of 13,14-dihydro-17-phenyl-18,19,20-trinor-PGE₁

(Refer to formula VI wherein

M is H  OH,

Q is —(CH₂)₂—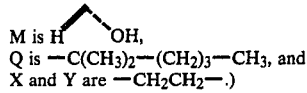, and

X and Y are —CH₂CH₂—.)

| Example | Phenacyl Halide | Product 13,14-dihydro-17-phenyl-18,19,20-trinor-PGE₁ ester of formula: |
|---|---|---|
| 106 | phenacyl bromide | VI-A |
| 107 | p-bromophenacyl bromide | VI-B |
| 108 | p-phenylphenacyl bromide | VI-C |
| 109 | p-nitrophenacyl bromide | VI-D |
| 110 | p-benzamidophenacyl bromide | VI-E |
| 111 | 2-bromo-2'-acetonaphthone | VI-F |
| 112 | 2-bromo-1,3-diphenyl-1,3-propanedione | VI-G |

I claim:

1. An optically active compound of the formula:

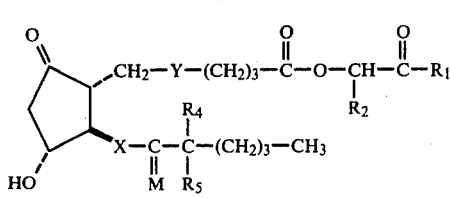

wherein each of $R_4$ and $R_5$ is hydrogen or methyl, being the same or different; wherein M is

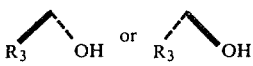

wherein $R_3$ is hydrogen or methyl; wherein $R_1$ is phenyl, p-bromophenyl, p-biphenylyl, p-nitrophenyl, p-benzamidophenyl, or 2-naphthyl; wherein $R_2$ is hydrogen or benzoyl; and wherein
  (a) X is —$CH_2CH_2$— or trans—CH=CH— and Y is —$CH_2CH_2$—, or
  (b) X is trans—CH=CH— and Y is cis—CH=CH—.

2. A compound according to claim 1 wherein X is trans—CH=CH— and Y is cis—CH=CH—.

3. A compound according to claim 2 wherein $R_4$ and $R_5$ are hydrogen.

4. A compound according to claim 3 wherein $R_3$ is hydrogen.

5. The phenacyl ester of $PGE_2$, a compound according to claim 4.

6. The p-bromophenacyl ester of $PGE_2$, a compound according to claim 4.

7. The p-phenylphenacyl ester of $PGE_2$, a compound according to claim 4.

8. The p-nitrophenacyl ester of $PGE_2$, a compound according to claim 4.

9. The p-benzamidophenacyl ester of $PGE_2$, a compound according to claim 4.

10. The 2-naphthoylmethyl ester of $PGE_2$, a compound according to claim 4.

11. The α-benzoylphenacyl ester of $PGE_2$, a compound according to claim 4.

12. A compound according to claim 3 wherein $R_3$ is methyl.

13. The p-phenylphenacyl ester of 15(S)-15-methyl-$PGE_2$, a compound according to claim 12.

14. The p-nitrophenacyl ester of 15(S)-15-methyl-$PGE_2$, a compound according to claim 12.

15. The p-nitrophenacyl ester of 15(R)-15-methyl-$PGE_2$, a compound according to claim 12.

16. A compound according to claim 2 wherein $R_4$ and $R_5$ are methyl.

17. The phenacyl ester of 16,16-dimethyl-$PGE_2$, a compound according to claim 16.

18. The p-phenylphenacyl ester of 16,16-dimethyl-$PGE_2$, a compound according to claim 16.

19. A compound according to claim 1 wherein X is trans—CH=CH— and Y is —$CH_2CH_2$—.

20. A compound according to claim 19 wherein $R_4$ and $R_5$ are hydrogen.

21. The p-phenylphenacyl ester of $PGE_1$, a compound according to claim 20.

22. A compound according to claim 19 wherein $R_4$ and $R_5$ are methyl.

23. The p-phenylphenacyl ester of 16,16-dimethyl-$PGE_1$, a compound according to claim 22.

24. A compound according to claim 1 wherein X and Y are —$CH_2CH_2$—.

25. A compound according to claim 24 wherein $R_4$ and $R_5$ are hydrogen.

26. The p-phenylphenacyl ester of 13,14-dihydro-$PGE_1$, a compound according to claim 25.

27. A compound according to claim 24 wherein $R_4$ and $R_5$ are methyl.

28. The p-phenylphenacyl ester of 16,16-dimethyl-13,14-dihydro-$PGE_1$, a compound according to claim 27.

29. Free-flowing crystals of a compound of the formula:

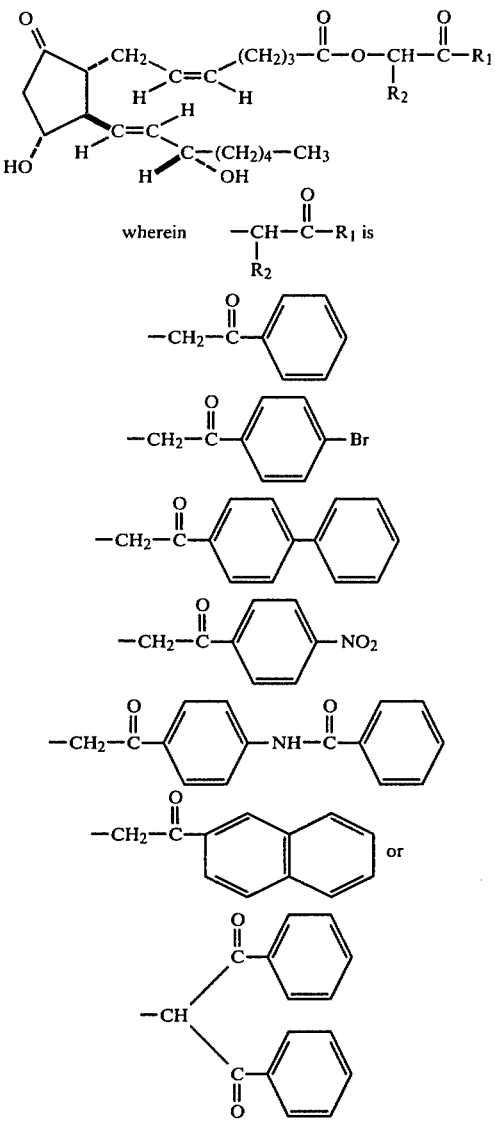

30. An optically active compound of the formula

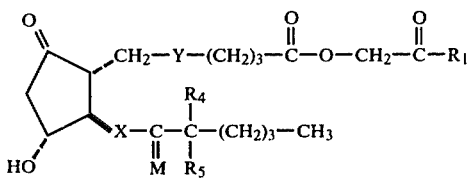

wherein each of $R_4$ and $R_5$ is hydrogen or methyl, being the same or different; wherein M is

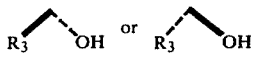

wherein $R_3$ is hydrogen or methyl; wherein $R_1$ is phenyl, p-bromophenyl, p-biphenylyl, p-nitrophenyl, p-benzamidophenyl, or 2-naphthyl; and wherein (a) X is —$CH_2CH_2$— or trans—CH=CH— and Y is —$CH_2CH_2$—, or (b) X is trans—CH=CH— and Y is cis—CH=CH—.

* * * * *

UNITED STATES PATENT OFFICE
CERTIFICATE OF CORRECTION

Patent No. 4,304,926           Dated 8 December 1981

Inventor(s) Walter Morozowich

It is certified that error appears in the above-identified patent and that said Letters Patent are hereby corrected as shown below:

On the title page,
Title, "PGE-TYPES" should read -- PGE-TYPE --.
Column 10, line 33, "(7.3))" should read -- (7:3)) --.

Signed and Sealed this

Twenty-eighth Day of December 1982

[SEAL]

Attest:

GERALD J. MOSSINGHOFF

Attesting Officer     Commissioner of Patents and Trademarks